May 18, 1976 J. W. HINES, Jr. Plant Pat. 3,887
PYRACANTHA PLANT
Filed Nov. 25, 1974
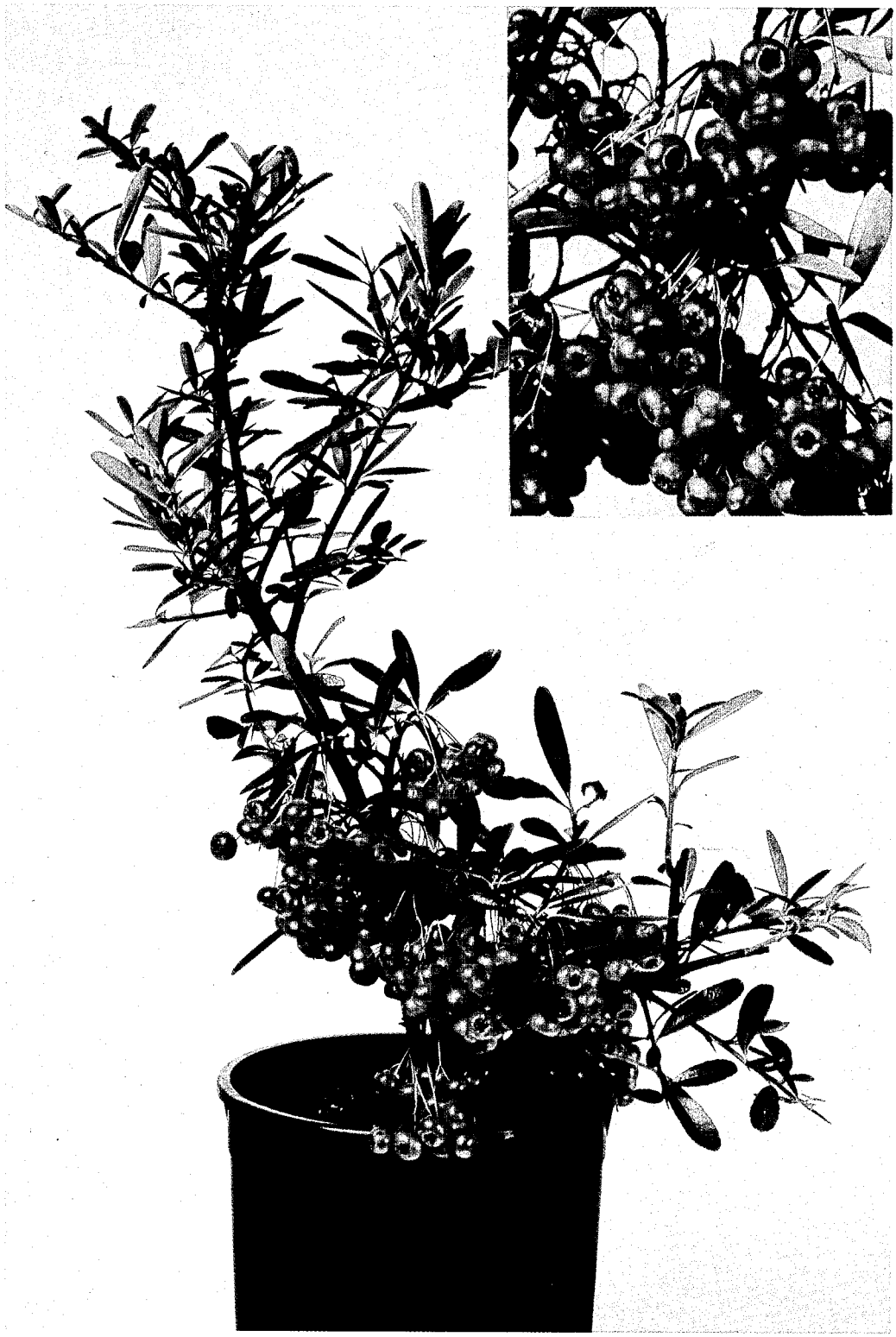

United States Patent

Plant Pat. 3,887

Patented May 18, 1976

3,887

PYRACANTHA PLANT

James W. Hines, Jr., Corona Del Mar, Calif., assignor to Hines Wholesale Nurseries, Santa Ana, Calif.

Filed Nov. 25, 1974, Ser. No. 526,638

Int. Cl. A01h 5/00

U.S. Cl. Plt.—54 1 Claim

The present invention relates to a new and distinct variety of pyracantha plant. I discovered this new variety on my cultivated property at 12621 Jeffrey Road, in the city of Santa Ana, county of Orange, State of California, in the late fall of 1971. This new variety originated as a seedling growing in a bed of *Pyracantha fortuneana* "Graberi," an unpatented variety.

My discovery of this seedling was accasioned by the fact that at the time aforementioned, I was growing a great many pyracantha of the variety *P. fortuneana* "Graberi" under my direction and control in the nursery of my assignee, located in Santa Ana, Calif., in which I held and still hold a partnership interest. While observing and supervising the growth and cultivation of these plants, I observed that one plant in particular, while it had growth characteristics similar to other plants around was slightly to the side of the planting bed rows, and bore fruit that was a much darker shade of red than other plants around it. I isolated the plant and took numerous cuttings from it. I kept the mother plant and the cuttings made therefrom under close observation. The outstanding color characteristics of the fruit of this seedling and the fruit of the cuttings therefrom were confirmed by these tests; i.e. the color variation referred to remained true for succeeding generations, through asexual reproduction. Plants grown from seed, however, bore fruit dissimilar in color from fruit of the plant which is specified in this petition.

In the accompanying drawing a young plant is shown, together with an insert photograph of fruit clusters. The fruit as illustrated is slightly less than life-size. The color of fruit in the drawing is somewhat lighter than actual, but is depicted in color as nearly true as reasonably possible to reproduce in a photograph of this type.

To facilitate identification of the important colors, I have used the color terminology of the R.H.S. Colour Chart of the Royal Horticultural Society of London.

Locality where grown and observed: The Irvine Ranch, approximately 5 miles south of Santa Ana, Calif.

Parentage: Chance seedling.

*Seed parent.*—*Pyracantha fortuneana* "Graberi."

*Pollen parent.*—Unknown.

THE PLANT

Growth: Pyracantha (commonly called Firethorn) is an ornamental shrub grown chiefly for the display in the Spring of masses of white flowers which turn in the fall and winter to colorful berry-like fruit. According to variety, fruit colors range from orange through coral red to bright red. To my knowledge, the plant specified herein is the first break-through to a shade of red so dark that the clusters of berries appear to be cherries. Since the seedling was first discovered by me in the fall of 1971, and first bloomed in the spring of 1972 (under my personal observation), the ultimate height and spread is unknown. It is believed, however, that since growth to date has shown the plant to be a vigorous upright grower, it should retain the characteristics of its seed parent and possibly attain a height of 10 to 15 feet, and be hardy through winter periods as low as Zone 7 of the Plant Hardiness Zone Chart of the U.S. National Arboretum (0° to 10°).

Branches: Older branches are in the Greyed-Green Group, Plates 197A and 197B. These colors blend to the mature branches, with colors in the Brown Group, Plates 200B to 200C. New branches are in the Greyed-Red Group, ranging in color from Plate 178A where joined to a mature branch, and lightening to Plates 178B, 178C and 178D at the tips. Spines appear on the branches, and are ⅜ to ½ inch in length.

Foliage: Leaves are semi-glossy, of good substance, and of medium abundance. They are alternate in groups of 3 to 4.

Shape: Linear to oblanceolate, with an obtuse tip. Some leaf edges are crenate.

Color:

*New leaves.*—Surface is in the Green Group, Plates 143B to 143C. Underside is in the Yellow-Green Group, Plate 144A. However, very young leaves at the tips of new growth are present in 6 to 8 pairs of leaves, with coloration in the Greyed-Orange Group, Plates 172A to 172B.

*Mature leaves.*—Surface is in the Yellow-Green Group, Plates 147A to 147B. Underside is in the Yellow-Green Group, Plates 148B to 148C.

Size: Young and new leaves are from ⅛ to ½ inch in width, and from ⅜ to 1⅞ inches in length. Mature leaves are from ⅜ to ⅝ inches in width, and from 1⅜ to 2¾ inches in length.

Veins: Mid-vein is prominent and lighter in color than the leaf, running from the petiole to the tip, and having pinnate veins extending therefrom.

THE FLOWER

The plant first flowers from February to March, with heaviest blooming in late March to early April. The flowers appear in numerous corymbs, followed by the fruit. Flowers are in the White Group, Plates 155B to 155C. They are very numerous.

THE FRUIT

Aside from the decorative value of pyracantha as an ornamental shrub with masses of white flowers in the spring, they are chiefly grown for their colorful berry-like fruit in the fall and winter. The fruit will remain on the branches all winter if not eaten by birds.

Color: Color of the fruit is in the Red Group, Plate 46A, quite similar to cherries in coloration.

Size: From 5/16 to ⅝ inches in width, and from ¼ to ⅜ inches in height.

Shape: Depressed-globose.

I claim:

1. A new and distinct variety of Pyracantha with white flowers, characterized particularly as to novelty by the cherry-like color of its fruit.

No references cited.

ROBERT E. BAGWILL, Primary Examiner